United States Patent [19]

Shigemitsu

[11] Patent Number: 6,165,775
[45] Date of Patent: Dec. 26, 2000

[54] BACILLUS DECOMPOSING TURF PSEUDO THATCH AND THATCH, AND A MICROBIAL MATERIAL CONTAINING THE BACILLUS

[75] Inventor: Haruhiro Shigemitsu, Aichi, Japan

[73] Assignee: Asada Corporation, Tokyo, Japan

[21] Appl. No.: 09/277,079

[22] Filed: Mar. 26, 1999

[51] Int. Cl.[7] .............................. B09B 3/00; C12N 1/00; C12N 1/20
[52] U.S. Cl. .................... 435/252.5; 435/262.5; 435/832; 435/9; 424/93.46
[58] Field of Search ............... 435/252.1, 262.1, 435/822, 832, 262.5, 252.5; 424/93.46

[56] References Cited

U.S. PATENT DOCUMENTS

| | | | |
|---|---|---|---|
| 4,952,229 | 8/1990 | Muir | 71/7 |
| 5,401,709 | 3/1995 | Andriollo et al. | 504/117 |
| 5,527,526 | 6/1996 | Crawford | 424/93.43 |

*Primary Examiner*—David M. Naff
*Assistant Examiner*—Deborah K. Ware
*Attorney, Agent, or Firm*—Fish & Richardson PC

[57] ABSTRACT

There are provided *Bacillus macerans* decomposing turf pseudo thatch and thatch, a microbial mixture composition comprising 1 part by weight of the Bacillus microorganism and 5 to 30 parts by weight of clay minerals, and a microbial material comprising at least one compound selected from the group consisting of 50 to 100 parts by weight of an ionic surfactant, 50 to 100 parts by weight of casein and 50 to 100 parts by weight of a casein hydrolyzate, and 50 to 200 parts by weight of sugars, in 100 parts by weight of said microbial mixture composition. This microbial material decomposes thatch by transferring not only to turf pseudo thatch but also to the soil, also decomposes pseudo thatch layers without exerting any adverse effect on the soil and environments for living creatures, and in golf courses, can promote growth of turf.

9 Claims, No Drawings

BACILLUS DECOMPOSING TURF PSEUDO THATCH AND THATCH, AND A MICROBIAL MATERIAL CONTAINING THE BACILLUS

FIELD OF THE INVENTION

The present invention relates to Bacillus having the ability to decompose turf pseudo thatch and/or thatch and to a microbial material comprising said Bacillus as an active ingredient.

BACKGROUND OF THE INVENTION

In places with turf such as gardens and the green in golf courses, it is necessary to trim turf at predetermined intervals, and turf pseudo thatch is thus generated. Further, turf when partially withered and dead should be removed together with roots.

If these residues such as turf pseudo thatch, withered roots, crown portions, subterranean stems and branched stems are accumulated in the soil for a prolonged period of time, thatch layers are formed. Further, turf pseudo thatch is accumulated on turf on the surface of the earth, and a layer called pseudo thatch is thus formed.

Such pseudo thatch forms a hotbed in which various microorganisms including various pathogenic fungi overgrow. In particular, in the case of pathogenic fungi forming spores, it is known that spores serve as a new inoculation source of these pathogenic fungi.

If the thatch layer exceeds 2 cm, the formation of turf in golf courses and the decomposition process thereof in an ecological system are unbalanced, and simultaneously the transfer of water, air, fertilizers or agricultural chemicals to the soil is prevented. Further, it is known that diffusion of carbon dioxide and other gases from the soil is also prevented.

To reduce the thickness of the thatch layer, measures such as vertical treatment, aeration in spring and autumn and application of suitably grained soil are taken, but their effects are hardly obtained.

Accordingly, it is an urgent task to develop materials for decomposition of thatch, and it is also desired that these materials do not cause environmental pollution.

SUMMARY OF THE INVENTION

As a result of their eager study for solving the problem described above, the present inventors found that a microorganism of the genus Bacillus derived from fermented animal fertilizers has the ability to decompose cellulose and pectin of plants, and the present invention was thereby completed. Further, the inventors examined a combination of this microorganism and various compounds having a spread-promoting effect, so that the inventors arrived at a microbial material for promoting decomposition of thatch layers.

That is, the first mode of the present invention is *Bacillus macerans* having the ability to decompose cellulose and pectin. This *Bacillus macerans* is characterized by having the ability to decompose turf pseudo thatch and thatch.

Further, the second mode of the present invention is a microbial mixture composition comprising a microbial mixture with which clay minerals have been mixed in an amount of 5 to 30 parts by weight relative to 1 part by weight of said Bacillus microorganism.

Here, the clay minerals are characterized in that they act as a water absorbing agent.

The third mode of the present invention is a microbial material comprising at least one compound selected from the group consisting of 50 to 200 parts by weight of an ionic surfactant, 50 to 100 parts by weight of casein and 50 to 100 parts by weight of a casein hydrolyzate, relative to 100 parts by weight of the microbial mixture composition described above, and 50 to 200 parts by weight of sugars relative to 100 parts by weight of said microbial mixture composition.

Here, said sugars are one or more sugars selected from the group consisting of saccharose, glucose, lactose, fructose and maltose.

Further, said ionic surfactant is a surfactant selected from the group consisting of a cationic surfactant, an anionic surfactant and an amphoteric surfactant. Said cationic surfactant is preferably cetyltrimethylammonium bromide or dodecyltrimethylammonium bromide, and said anionic surfactant is preferably an alkyl sulfate or an alkyl benzene sulfonate. Further, said amphoteric surfactant is characterized in that it is at least one surfactant selected from the group consisting of lecithin, lysolecithin and phosphatidylethanolamine.

In addition, said casein hydrolyzate is characterized in that it is peptone or casamino acid.

DETAILED DESCRIPTION OF THE INVENTION

Hereinafter, the microorganism and microbial material of the invention for decomposition of turf pseudo thatch and/or thatch are described in detail.

The *Bacillus macerans* of the invention is a microorganism obtained from animal organic fertilizers during fertilization. This *Bacillus macerans* can be obtained by screening in the following method. That is, a suitable amount of water is mixed with a meat and bone animal organic fertilizer containing 10% dried blood and accumulated in a concrete frame to promote fermentation.

When the fermentation temperature is raised to about 50° C. or more, preferably about 60 to 70° C., the fermented animal organic fertilizer is collected from a depth of about 30 cm under the surface layer. This collected fertilizer is diluted at 5-to 500,000-fold, preferably 100,000, in sterilized water and screened by a dilution plate method whereby the microorganism is obtained.

This screening is conducted in the following manner. For screening, 2 kinds of media, that is, a plate agar medium (DIFCO) placed in a petri dish and a slant medium in a test tube, are used. Although the medium for screening may be any commercial medium, a nutrient medium is preferable because it contains an animal beef extract.

The above diluted fluid is applied to this plate agar medium by e.g. a cone large bar and cultured in a thermostatic chamber at a suitable temperature e.g. about 30° C. for e.g. about 120 to 168 hours until the microorganism in the diluted fluid is grown.

The microorganism grown in this plate agar is isolated by means of e.g. Ase, transferred to the slant medium prepared as described above, and cultured under the same conditions as in the plate agar medium.

The microbial properties of the microorganism grown in the slant medium are examined by standard methods described in Bergey's Manual, Cowan and Steel's, etc. to identify the microorganism, and the microorganism thus identified is examined for the ability to decompose cellulose and pectin as well as for the ability to decompose turf pseudo thatch.

The microorganism of the invention can be grown in media generally used for microbial culture. Such media include e.g. nutrient medium, peptone medium, yeast extract/albumin medium, yeast extract/mannitol medium, and potato broth medium.

The ability to decompose cellulose can be examined in terms of the ability to disintegrate a filter paper, and reduction in the anti-tension, loss in weight, formation of reducing sugar or reduction in viscosity of water-soluble cellulose derivative (CMC) etc. as the substrate, among which the method of examining the ability to disintegrate a filter paper is preferable because the filter paper is close to natural cellulose.

Specifically, a predetermined medium is introduced into an L-shaped tube, sealed and sterilized in an autoclave. A filter paper sterilized under dry conditions is cut into pieces of a predetermined size, then a plurality of the pieces are introduced into it, a predetermined amount of *Bacillus macerans* is inoculated into it and cultured for a predetermined period of time in a thermostatic shake incubator, and the state of disintegration of the filter paper is examined. The L-shaped tube can be a commercial product, for example, having an inner diameter of 15 mm to 25 mm, a vertical height of 40 to 45 mm, and a horizontal length of 140 to 150 mm. The medium includes the above media, among which a peptone liquid medium is preferably used because the number of microorganisms to be grown therein is high.

The filter paper sterilized under dry conditions is cut into pieces having e.g. a size of about 1×1 cm so that they are sufficiently shaken in the medium in the L-shaped tube.

A suitable amount of the medium is introduced into an L-shaped tube, and the microorganism is inoculated into it in an amount of about $2\times10^7$ to $8\times10^7$ cfu/ml and cultured whereby the ability to decompose cellulose can be evaluated clearly and accurately.

Because the decomposition of cellulose by the microorganism is actually conducted outdoor, the temperature shall be about 25 to 35° C., preferably about 30° C. In addition, because the decomposition needs time, the culture time is preferably about 20 to 40 days, more preferably about 30 days.

The ability to decompose cellulose is evaluated by visually judging the state of disintegration of each filter paper after culture.

The ability to decompose pectin is evaluated by pectinase activity assay using a plate (plate check). First, an agar medium containing polygalacturonic acid at a predetermined concentration is poured into a vessel to prepare a plate medium. A microorganism to be examined for pectinase activity is pre-cultured in a suitable liquid medium. A disk is soaked with a predetermined amount of this pre-culture and placed on the above plate medium, and this vessel is cultured at a predetermined temperature for a predetermined period of time to form colonies.

For example, the microorganism of this invention is pre-cultured in a nutrient medium, and a disk is soaked with about 0.5 ml of this culture, and this disk is placed on the above plate medium and cultured at about 30° C. for 96 hours or so to form colonies.

After the colonies are formed, an acid at a suitable concentration (for example, 5 N $H_2SO_4$) is added in a predetermined amount (for example, about 400 μl/vessel) and left at room temperature.

If the microorganism having formed colonies has pectinase activity, the circumference of the colonies is transparent, so by using this as an indicator, the presence or absence of the activity can be judged and evaluated with the eye.

The ability of the microorganism of the invention to decompose thatch is tested by using turf pseudo thatch. The turf pseudo thatch (leaves and stems) is cut with a suitable instrument into pieces of a predetermined size and air-dried at room temperature. A predetermined amount of the cut pseudo thatch is introduced into an Erlenmeyer flask, and a solution containing sucrose at a predetermined concentration is poured into the flask. This flask is sterilized in an autoclave and weighed, and the microorganism is added thereto and cultured for a predetermined period of time. The weight after culture is determined, and its dry weight is further determined to examine the ability to decompose thatch.

The turf is cut into pieces having sizes of about 0.5 to 1.5 cm, preferably about 1 cm. If the ability to decompose thatch is examined in a 200 ml Erlenmeyer flask, this turf pseudo thatch, about 1 to 10 g, preferably 2 to 5 g, is introduced into the flask, and about 0.5% aqueous glucose solution, preferably about 10 ml, is introduced into the flask such that the turf is immersed in it, and the flask is sealed and sterilized in an autoclave.

After this sterilization, a predetermined amount of the pre-cultured microorganism is inoculated into the medium and cultured. In consideration of actually used conditions, the culture temperature is preferably about 20 to 30° C., more preferably about 24° C. The culture period is about 30 to 90 days, preferably about 60 days.

After culture, the content of the flask is divided and dried by a warm-air dryer, and the weight is measured, and the reduction in the weight of the pseudo thatch after culture is determined. The reduction in the weight can be evaluated with good reproducibility by drying with warm air at about 60 to 80° C., preferably about 70° C., for about 7 days. Because the reduction in the weight indicates the decomposition of turf pseudo thatch, the reduction of the weight can be used as the indicator for evaluating the ability to decompose thatch.

The *Bacillus macerans* microorganism of the invention can be obtained by liquid culture and/or solid culture. In the case of liquid culture, any media generally used for microbial culture can be used. Such media include nutrient medium, peptone medium, yeast extract/albumin medium, yeast extract/mannitol medium etc.

In the case of solid culture, sterilized rice bran, rice bran, grains etc. can be used as the solid medium. The sterilized rice bran can be preferably used because it is inexpensive, easily available, and readily ground in preparing the microbial mixture composition or the microbial material described below.

In the case of liquid culture, shake culture by a shaker or stirring culture by a jar fermenter is conducted. In the case of solid culture, stationary culture is conducted in e.g. an incubator.

If culture is conducted for about 5 days at a culture temperature of about 25 to 35° C., preferably about 30° C., the yield of the microorganism is increased. In the case of liquid culture, the microorganism can be recovered by centrifugation at suitable ×g.

For example, if the *Bacillus macerans* of the invention is shake-cultured at 30° C. for 5 days and then centrifuged at 5000 rpm (4,620×g) for 15 minutes, about 0.5 g of the microorganism can be obtained from 100 ml of the culture.

Solid culture is conducted e.g. in the following manner. The *Bacillus macerans* of the invention is pre-cultured by shake culture at about 30° C. for 3 days in a peptone medium, and this culture is inoculated into the sterilized solid medium described above. The inoculation amount is about 5 to 15% (w/w), preferably about 10% of the solid medium. The medium after inoculation is further cultured at 30° C. for 4 days whereby a composition containing the microorganism can be obtained.

In the case of solid culture, separation of the microorganism from the culture is not conducted, and the culture itself is used for preparation of the microbial mixture composition of the invention.

One part by weight of the microorganism obtained by liquid culture as described above is mixed with 5 to 30 parts by weight of clay minerals. The clay minerals to be mixed act as an water-absorbing agent for absorbing water in the microorganism, thus facilitating dispersion of the microorganism in the microbial mixture composition. Such clay minerals include white clay, kaolin, diatomaceous earth, bentonite, zeolite etc. These clays may be mixed alone with the microorganism or may be used in combination thereof.

Although the mixing ratio of the water absorbing agent to the microorganism varies depending on the water content of the microorganism, the water absorbing agent is mixed in an amount of preferably 5 to 30 parts, more preferably 10 to 25 parts by weight relative to 1 part by weight of the microorganism to facilitate dispersion of the microorganism so that the ability of the microorganism to decompose thatch is sufficiently demonstrated. It is mixed most preferably in an amount of 15 parts by weight.

In the case of solid culture, 50 parts by weight of the solid medium containing the microorganism cultured in the manner described above is mixed with 50 parts by weight of the water-absorbing agent without separating the microorganism from the solid medium as described above.

When the microorganism and the water absorbing agent are mixed to prepare a microbial mixture composition, lumps are formed so this composition is pulverized. For pulverization of the composition, any grinder may be used insofar as the composition can be ground uniformly, and specifically, a homogenizer, a pot mill, a Waring blender etc. can be used.

The microbial material of the invention contains 100 parts by weight of said microbial mixture composition, 50 to 200 parts by weight of sugars, and 50 to 200 parts by weight of an ionic surfactant. By adding the sugars and the surfactant herein used, the microbial mixture composition of the invention spreads uniformly over turf and transfer thereof to the soil is also promoted. Further, because of the locations where these compounds are used, they serve as a nutrient source for growth of *Bacillus macerans*, and these should not be toxic to the human body.

As the sugars used in the present invention, saccharose, glucose, lactose, fructose, maltose etc. can be exemplified. These sugars can be used alone or in combination thereof, and saccharose and/or glucose is preferably used because these have a high spread-promoting effect as a leaf-sprayed fertilizer and are low molecules easily utilized by the microorganism.

Among a group of surfactant which can, in a small amount, change various properties of interfaces or surfaces, the ionic surfactant refers to that dissociating into ions when dissolved in water. Depending on the type of charge upon dissociation, the ionic surfactant is divided into anionic surfactant, cationic surfactant, and amphoteric surfactant.

Any of the ionic surfactants can be used in the present invention, and specifically the anionic surfactant includes sodium alkyl sulfate or alkyl benzene sulfonate, the cationic surfactant includes cetyltrimethylammonium bromide or dodecyltrimethylammonium bromide, and the amphoteric surfactant includes lecithin, lysolecithin and phosphatidylethanolamine.

These surfactants may be used alone or as a mixture thereof. Lecithin, particularly soybean lecithin, is preferably used because it is digestible, utilized in foods and highly safe.

The bacterial material of the invention is prepared by mixing 50 to 200 parts by weight of said sugars and 50 to 200 parts by weight of the ionic surfactant with 100 parts by weight of said microbial mixture.

The mixing ratio of 50 to 200 parts by weight of the sugars to 100 parts by weight of the microbial mixture is preferable for promotion of growth of the *Bacillus macerans* of the invention. Further, the mixing ratio of 50 to 200 parts by weight of the ionic surfactant is preferable for dispersing and spreading the microbial material of the invention.

If the mixing ratio each of the sugars and the ionic surfactant is about 100 parts by weight, the *Bacillus macerans* grows rapidly and its ability to decompose thatch is high. Most preferably, 100 parts by weight of the sugars and 100 parts by weight of the amphoteric surfactant are mixed with 100 parts by weight of the above microbial mixture composition.

Another microbial material of the invention contains 50 to 100 parts by weight of casein or its hydrolyzate in 100 parts by weight of the microbial mixture and 50 to 200 parts by weight of the sugars.

Casein is a protein occurring in milk, beans etc. and contains serine phosphate, and the casein hydrolyzate contains various components from casein digested with acids or enzymes. Specifically, casamino acid as an acid hydrolyzate, or peptone obtained by decomposition with an enzyme such as pepsin, can be mentioned.

Both casein and the casein hydrolyzate, when incorporated into the microbial material of the invention, have the effect of promoting the spreading of the microbial material over the surface of leaves and stems. Further, these ingredients are incorporated along with sugars to promote multiplication and growth of the *Bacillus macerans* of the invention and to raise the effect of decomposing turf pseudo thatch and/or thatch.

Preferably, the microbial material of the invention is prepared by uniformly mixing 100 parts by weight of the microbial mixture composition, about 100 parts by weight of sugars and about 100 parts by weight of casein or a casein hydrolyzate.

Although application amount of the microbial material of the invention varies depending on the amount of pseudo thatch, thickness of thatch layers, application time and application site, when the microbial material is diluted with water preferably at 1000- to 4000-fold in view of the effect.

That is, about 1.0 to 0.25 g of the microbial material of the invention is diluted with 1000 ml water and can be applied in an amount of 1000 to 2000 $ml/m^2$, and it is applied preferably in an amount of about 0.5 $g/m^2$/2000 ml.

The microbial material of the invention is applicable when soil temperature is 10° C. or more. Usually, it is applied once in spring and autumn respectively, and preferably it is further applied once in summer, particularly in the rainy season in summer.

EXAMPLES

Hereinafter, the present invention is described in detail by reference to the Examples, which however are not intended to limit the present invention.

Example 1

Screening and Identification of *Bacillus macerans*

(1) Screening of *Bacillus macerans*

About 10% water was added to and mixed with 5 tons of a meat bone powder organic fertilizer containing 10% dried blood (Aminaka Sangyo K. K.) and accumulated in a concrete frame with a size of about 2.0 m width×about 1.5 m depth×about 2.0 m height to promote fermentation, and a fermented animal fertilizer was thereby prepared.

When the fermentation temperature reached about 60 to 70° C. about 72 hours after accumulation, the fermented animal fertilizer was collected from a depth of 30 cm below the surface layer and diluted about 100,000-fold with sterilized water.

(2) Identification of *Bacillus macerans*

A nutrient agar medium (DIFCO) was introduced into a vessel with an inner diameter of 8.5 cm to prepare a plate agar medium. One ml of the diluted liquid prepared in item (1) above was introduced into it, applied throughout it by means of a cone large bar, and cultured in an incubator at 30° C.

Separately, the above nutrient medium was introduced into a test tube to prepare a slant medium.

120 to 168 hours after culture was initiated, a colony appeared on the nutrient plate agar medium. This colony was inoculated via a platinum loop into the slant medium. This slant medium was cultured at 30° C. similarly to the culture in the plate agar medium. The microbial properties of the microorganism thus isolated were examined and shown in Table 1.

TABLE 1

| | |
|---|---|
| 1. Morphological properties | |
| Size of the cell: | 0.5–0.7 × 2.5–5.0 μm |
| The presence or absence of spores: | Bacillus with spores |
| 2. Cultural properties (cultural states in the nutrient medium) | |
| Form of the colonies: | rough |
| Color: | cream color |
| Gloss: | — |
| Growth temperature | |
| Maximum: | 45–50° C. |
| Minimum: | 5–10° C. |
| 3. Physiological properties | |
| Attitude toward oxygen: | facultative anaerobic bacterium |
| Gram stainability: | + |
| Hemolysis: | β-hemolysis |
| Products from glucose | |
| Acid: | + |
| Gas: | + |
| Acetone (VP): | − |
| Acid from hydrocarbons | |
| Galactose: | + |
| Mannose: | + |
| Xylose: | + |
| ONPG: | + |
| Utilization of citric acid: | − |
| Urease: | − |
| Hydrolysis of starch: | + |
| Oxidase: | + |
| Escrine: | + |
| Reduction of nitrates: | + |

Identification of the microorganism shown in Table 1 was conducted in methods described in Bergey's Manual and Cowan and Steel's.

On the basis of the microbial properties shown in Table 1, the above microorganism was identified as *Bacillus macerans*. This microorganism (FERM BP-6680) was deposited on Aug. 21, 1996 with the Bioscience and Human-Technology, Agency of Industrial Science and Technology, Japan.

Example 2

Examination of the Ability of the Separated Microorganism to Decompose Cellulose The name "*Bacillus macerans*" thus identified contains "macerans" meaning "softening by steeping, retting", so this microorganism was examined for the ability to decompose cellulose and pectin in the following manner.

The ability to decompose cellulose was examined in terms of the ability of this microorganism to disintegrate a filter paper. That is, 5 ml peptone liquid medium was introduced into an L-shaped tube (made of glass, with an inner diameter of 18 to 19 mm, a vertical height of 40 to 45 mm and a horizontal length of 143 to 148 mm) for a Monod-type thermostatic shaker, then sealed with a silicon cap and sterilized at 121° C. for 20 minutes.

Filter paper (Toyo Filter No. 2 (1×1 cm)) was sterilized at 120° C. for 1 hour under dry conditions, and 3 filter paper pieces were added to the above L-shaped tube containing the sterilized medium. The microorganism was subjected to shake culture in a thermostatic water bath at 30° C. for 30 days, and the state of disintegration of the filter paper pieces was examined and evaluated with the eye. As the judgement criteria, ++ was assigned to the complete disintegration of the filter paper pieces into fibers, + was assigned to the partial disintegration of the filter paper pieces or disintegration of the circumference thereof, and − was assigned to the original unchanged state. The results are shown in Table 2.

TABLE 2

Disintegration power of the genus Bacillus toward filter paper pieces

| Species of the genus Bacillus | Disintegration Power |
|---|---|
| Bacillus macerans | ++ |
| Bacillus licheniformis | − |
| Bacillus subtilis | − |
| Bacillus amyloliquefaciens | + |
| No microorganism | − |

Example 3

Examination of the Ability of the Separated Microorganism to Decompose Pectin

The microorganism isolated and identified in Example 1 was examined for its ability to decompose pectin by the plate method using pectinase activity as the indicator in the following manner.

(1) Preparation of PYA Plate 0.7 g of polygalacturonic acid (derived from orange, 85 to 90% purity, a product of Sigma) and 1.0 g yeast extract (Difco) were dissolved in 70 ml deionized water. This solution was adjusted to pH 5.3 with dilute hydrochloric acid, and 1 g agar was added to it, and the volume was adjusted to 100 ml.

This agar solution was sterilized at 121° C. for 1 minute, and after sterilization, the flask was inclined to be left so that insolubles settled at the bottom. This supernatant was poured into 5 petri dishes of 8.5 cm diameter to prepare agar plates which were then dried.

(2) Culture of the Bacillus Microorganism

The same four species of the genus Bacillus as in Example 2 were inoculated at $2-5\times10^7$ cfu microorganisms/ml into the same nutrient medium as in Example 1 and pre-cultured at 30° C. for 96 hours. Then, 0.5 ml of each of the cultured microorganisms of the genus Bacillus was soaked in each of filter disks of 8 mm in diameter sterilized under dry conditions (sterilization conditions: 180° C., 60 minutes).

The 3 filter disks were placed on the PYA plates prepared in item (1) above and cultured at 30° C. for 96 hours to form colonies.

(3) Assay of Pectinase Activity

400 μl of 5 N sulfuric acid was introduced into each vessel and left at room temperature. If there was pectinase activity, the circumference of the formed colonies became transparent, and + was assigned to this case, and − was assigned to a non-transparent case. The results are shown in Table 3.

TABLE 3

| Species of the genus Bacillus | Pectinase activity |
| --- | --- |
| Bacillus macerans | + |
| Bacillus licheniformis | + |
| Bacillus subtilis | + |
| Bacillus amyloliquefaciens | + |
| No microorganism | − |

It was found that all of the four species of the genus Bacillus indicate + and have pectinase activity.

Example 4

Ability to Decompose Turf Pseudo Thatch

The ability to decompose turf pseudo thatch was examined in the following test.

Creeping bentgrass and Kentucky blue grass, grown in a garden at home, until their height reached about 10 cm, were trimmed to a height of 2 cm, and the turf removed by trimming was dried for 3 days in the sun. The dried turf was passed through a sieve to remove sand, and only the turf pseudo thatch was collected, cut with turf scissors into pieces with a Length of about 1 cm, and air-dried at room temperature for 14 days.

The air-dried turf pseudo thatch, i.e. 5 g of creeping bentgrass and 2 g of Kentucky blue grass were introduced separately into ten 200-ml Erlenmeyer flasks. Ten ml of 0.5% glucose solution was quietly poured into each flask and sealed with a silicon cap to flatten the pseudo thatch in the flask, and sterilized in an autoclave at 121° C. for 20 minutes.

After cooling, each flask was weighed, and 1 ml of each of the test microorganisms previously cultured in a nutrient liquid medium was inoculated into each flask. In the control section for comparison, 1 ml of each of the Bacillus species shown in Example 2 was inoculated. In the section of no microorganism, 1 ml of sterilized water was inoculated. The test species are shown in Table 3. The flasks in the test section and the control section were incubated in an incubator at 24° C. for 60 days (n=2).

After 60 days, each flask was weighed. The content of the flask was divided, dried for 7 days under an air stream with a warm-air dryer at 70° C. until its weight became constant, and weighed, and the ability of each of the inoculated species to decompose pseudo thatch was evaluated. The ability to decompose the pseudo thatch of the creeping bentgrass is shown in Table 4, and the ability to decompose Kentucky blue grass is shown in Table 5.

TABLE 4

Ability of test species of genus Bacillus to decompose pseudo thatch of creeping bentgrass

| Test species | Weight before culture (g) | Weight after culture (g) | Weight after drying (g) | Weight of silicon cap + flask (g) | Reduction in dry weight (1 (g) | Substantial reduction in dry weight (2 (g) |
| --- | --- | --- | --- | --- | --- | --- |
| none | 125.337 | 121.940 | 115.449 | 110.704 | 4.741 | |
| | 130.288 | 127.848 | 120.561 | 115.796 | 4.765 | |
| | | | | | 4.753 (3 | — |
| Bacillus macerans | 129.293 | 123.392 | 116.849 | 114.986 | 1.863 | |
| | 133.456 | 128.821 | 120.891 | 118.996 | 1.895 | |
| | | | | | 1.879 (3 | 2.874 |
| Bacillus licheniformis | 127.636 | 123.967 | 117.208 | 113.131 | 4.077 | |
| | 127.402 | 123.377 | 116.918 | 112.957 | 3.961 | |
| | | | | | 4.019 (3 | 0.734 |
| Bacillus subtilis | 129.414 | 125.739 | 118.806 | 114.854 | 3.955 | |
| | 122.427 | 118.417 | 111.794 | 107.880 | 3.914 | |
| | | | | | 3.914 (3 | 0.818 |
| Bacillus amyloliquefaciens | 129.963 | 124.860 | 118.435 | 115.481 | 2.954 | |
| | 133.456 | 129.062 | 121.891 | 118.996 | 2.895 | |
| | | | | | 2.925 (3 | 1.828 |

(1: Weight of dry weight after culture minus (flask weight + silicon cap weight)
(2: Difference between reduction of dry weight and reduction of dry weight measured in the section inoculated with only sterilized water (control section)
(3: Average values

TABLE 5

Ability of test species of genus Bacillus to decompose pseudo thatch of Kentucky blue grass

| Test species | Weight before culture (g) | Weight after culture (g) | Weight after drying (g) | Weight of silicon cap + flask (g) | Reduction in dry weight (1 (g) | Substantial reduction in dry weight (2 (g) |
|---|---|---|---|---|---|---|
| none | 123.831 | 120.342 | 114.659 | 112.685 | 1.974 | |
| | 124.641 | 121.347 | 115.502 | 113.633 | 1.869 | |
| | | | | | 1.922 (3 | — |
| Bacillus | 126.974 | 122.505 | 116.813 | 115.914 | 0.899 | |
| macerans | 130.032 | 127.093 | 120.307 | 119.497 | 0.810 | |
| | | | | | 0.855 (3 | 1.067 |
| Bacillus | 127.396 | 124.232 | 117.603 | 116.360 | 1.243 | |
| licheniformis | 128.452 | 124.905 | 118.671 | 117.423 | 1.248 | |
| | | | | | 1.248 (3 | 0.674 |
| Bacillus | 122.045 | 118.287 | 112.400 | 111.212 | 1.188 | |
| subtilis | 118.962 | 115.299 | 109.138 | 107.965 | 1.173 | |
| | | | | | 1.181 (3 | 0.741 |
| Bacillus | 124.631 | 121.247 | 114.902 | 113.899 | 1.003 | |
| Amyloliquefaciens | 124.860 | 121.435 | 114.762 | 113.697 | 1.064 | |
| | | | | | 1.034 (3 | 0.880 |

(1: Weight of dry weight after culture minus (flask weight + silicon cap weight)
(2: Difference between reduction of dry weight and reduction of dry weight measured in the section inoculated with only sterilized water (control section)
(3: Average values As shown in Tables 4 and 5, it was revealed that the substantial reduction in the dry weight is the largest in the section treated with the *Bacillus macerans* of the invention, indicating that this microorganism decomposes the turf pseudo thatch effectively.

Example 5

Preparation of a Composition Mixed with the *Bacillus macerans* Microorganism

The *Bacillus macerans* obtained in Example 1 was cultured at 30° C. for 5 days in a peptone liquid medium under stirring. The culture was transferred to a centrifuge tube and centrifuged at 5,000 rpm for 15 minutes, and the supernatant was discarded and the microorganism was collected. 0.4 to 0.6 g of the microorganism was obtained from 100 ml of the culture.

Fifteen parts by weight of bentonite were mixed with 1 part by weight of the resulting microorganism and stirred and ground by a grinder (Sample Mill SK-M10R, Tokyo Rika Co., Ltd.) to give the microbial mixture composition of the invention.

Example 6

Preparation of a Microbial Material Consisting of the Microbial Mixture Composition, a Sugar and a Surfactant 100 parts by weight each of saccharose and an amphoteric surfactant, soybean lecithin (Nakarai Tesque Co., Ltd. ) were mixed with 100 parts by weight of the microbial mixture obtained in Example 5, and the mixture was stirred uniformly in a stirrer (Mazera Z-1000, Tokyo Rika Co. , Ltd. ) whereby the microbial material 1 of the invention was obtained.

Example 7

Preparation of the Microbial Materials of the Invention Consisting of the Microbial Mixture Composition, a Sugar and a Casein Hydrolyzate Microbial material 2 containing 100 parts by weight of saccharose and 100 parts by weight of casein mixed with 100 parts by weight of the microbial mixture obtained in Example 5, microbial material 3 containing the same ingredients as above except for 100 parts by weight of peptone in place of casein, and microbial material 4 containing the same ingredients as above except for 100 parts by weight of casamino acid (Nakarai Tesque Co., Ltd.) in place of casein, and these were stirred uniformly in a stirrer (Mazera Z-1000, Tokyo Rika Co., Ltd.) to give the microbial materials 2 to 4 of the invention, respectively.

Example 8

Examination of Decomposition of Thatch

The microbial materials 1 and 2 obtained in Examples 6 and 7 were evaluated for the ability to decompose thatch in the following test.
(1) Preparation of an artificial thatch layer Creeping bentgrass grown in a garden at home until it reached a height of about 10 cm, was trimmed to 2 cm in height. The pseudo thatch of this bentgrass removed by trimming was dried for 3 days in the sun and then passed through a sieve to remove sand etc. whereby only the pseudo thatch was collected. This pseudo thatch was cut into pieces having a size of about 1 cm by means of rotational turf scissors (Arkland Sakamoto Co., Ltd.) and further dried at room temperature for 14 days.

Forty transparent plastic cylinders with an inner diameter of 11.3 cm and a height of 33 cm were prepared and covered at the bottom with a double-layered gauze which was fixed with a rubber tape, and each cylinder was packed with grain sand used for the green in golf courses.

Three round cut nets for window screens were placed respectively at a position 12 cm below from the upper portion of cylinders 1 to 20 and at a position 7 cm below from the upper portion of cylinders 21 to 40, and 2 g of the pseudo thatch was placed thereon to form a layer of uniform thickness. Three round cut nets for window screens were further placed thereon, and grain sand was placed thereon in a thickness of 10 cm for cylinders 1 to 20 and in a thickness of 5 cm for cylinders 21 to 40 to prepare an artificial thatch layer.

(2) Spraying of the Microbial Materials

All the cylinders containing this artificial thatch layer was sprayed with water in an amount of 4,000 ml/m² (40 ml per cylinder). Immediately thereafter, the microbial material 1 obtained in Example 6 and the microbial material 2 obtained in Example 7 were diluted at 2,000-fold (w/v) with water and sprayed in an amount of 2,000 ml/m² (20 ml per cylinder).

There is no commercial thatch decomposer available at present, so no positive control section was set up. In the negative control section, only water was sprayed. After spraying, it was left for 14 days in the shade under a concrete stand in a greenhouse.

(3) Confirmation of Transfer of the Microorganism from the Microbial Material to the Thatch Layer (soil)

To confirm whether the microorganism was transferred from the microbial materials 1 and 2 to the thatch layer (soil), the materials 1 and 2 were diluted 2,000-fold with which a cylinder containing a thatch layer of 5 cm in thickness prepared in the same manner as in item (1) above was sprayed in an amount of 2,000 mL/m² in the same manner as described above. Thereafter, it was left in the same manner as in item (2) above.

(4) Evaluation of the Effect of the Microbial Material on Decomposition of Thatch 14 days after spraying, pseudo thatch was recovered from each cylinder and dried for 2 days with a warm-air dryer at 80° C. Sand etc. adhering thereto were removed cleanly with tweezers, and the reduction in the dry weight was determined.

The difference between the reduction in the dry weight and the reduction in the dry weight measured in the water-sprayed section was regarded as the substantial reduction in the dry weight and evaluated as the ability to decompose thatch. The results are shown in Table 6.

TABLE 6

| | Ability to Decompose Thatch | | | | | |
| | Thatch layer 5 cm | | | Thatch layer 10 cm | | |
| Treatment | 1 | 2 | ratio | 1 | 2 | ratio |
| water spray | 1.830* | — | — | 1.895 | — | — |
| microbial mixture composition | 1.578 | 0.252 | 1.00 | 1.786 | 0.109 | 1.00 |
| microbial material 1 | 0.672 | 1.158 | 4.60 | 1.027 | 0.868 | 7.96 |
| microbial material 2 | 0.662 | 1.168 | 4.63 | 1.062 | 0.833 | 7.64 |

*: average in 5 cylinders
1: reduction in dry weight (g)
2: substantial reduction in dry weight (g)

As shown in Table 6, if the microbial mixture composition only was diluted and sprayed, the decomposition of the thatch layer was hardly observed. On the other hand, the microbial materials 1 and 2 of the invention showed a high ability to decompose both the thatch layers of 5 cm and 10 cm in depth.

(5) Transfer of the Microorganism into the Thatch Layer and Grain Sand

Further, it was examined whether the *Bacillus macerans* of the invention is isolated from the grain sand and thatch of 5 cm depth below the contact surface between the thatch layer and the grain sand. As a result, the *Bacillus macerans* was not detected in the section treated with the microbial mixture composition, while the *Bacillus macerans* was detected in any sections treated with the microbial materials of the invention. From the foregoing, it was found that the microorganism contained in the microbial materials 1 and 2 transfers to the soil.

According to the present invention, *Bacillus macerans* having the ability to decompose cellulose and pectin and decomposing turf pseudo thatch is provided, and a microbial mixture composition containing this microorganism is also provided.

A microbial material which decomposes thatch rapidly by transferring not only to turf pseudo thatch but also to the soil is provided by mixing compounds having a spread-promoting effect, such as sugars, ionic surfactants etc. with this microbial mixture composition.

The microbial material of the invention decomposes a pseudo thatch layer which is a source for forming spores of pathogenic fungi and a new inoculation source, without exerting any adverse effect on the soil and environments for living creatures, and in golf courses it can promote healthy growth of turf.

All publications, patents and patent applications cited herein are incorporated herein by reference in their entirety.

What is claimed is:

1. A microbial mixture composition consisting essentially of a biologically pure *Bacillus macerans* having the ability to decompose cellulose and pectin, and clay minerals.

2. A microbial mixture composition of claim 1, wherein said clay minerals have been mixed in an amount of 5 to 30 parts by weight to 1 part by weight of said *Bacillus macerans*.

3. A microbial material comprising 50 to 200 parts by weight of an ionic surfactant, 50 to 100 parts by weight of a casein hydrolyzate, 100 parts by weight of the microbial mixture composition described in claim 3, and 50 to 200 parts by weight of sugars.

4. A microbial material according to claim 3 wherein said casein hydrolyzate is peptone or casamino acid.

5. A microbial material according to claim 3 wherein said sugars are one or more sugars selected from the group consisting of saccharose, glucose, lactose, fructose and maltose.

6. A microbial material according to claim 3 wherein said ionic surfactant is a surfactant selected from the group consisting of a cationic surfactant, an anionic surfactant and an amphoteric surfactant.

7. A microbial material according to claim 6 wherein said cationic surfactant is cetyltrimethylammonium bromide or dodecyltrimethylammonium bromide.

8. A microbial material according to claim 6 wherein said anionic surfactant is an alkyl sulfate or an alkyl benzene sulfonate.

9. A microbial material according to claim 6 wherein said amphoteric surfactant is at least one surfactant selected from the group consisting of lecithin, lysolecithin and phosphatidylethanolamine.

* * * * *